(12) United States Patent
Huang et al.

(10) Patent No.: US 10,280,473 B2
(45) Date of Patent: May 7, 2019

(54) AUTOMATED HIV-1 VIRAL LOAD TESTING PROCEDURE FOR DRIED SPOTS

(71) Applicant: Abbott Molecular Inc., Des Plaines, IL (US)

(72) Inventors: Shihai X. Huang, Lincolnshire, IL (US); Chad Dunn, Chicago, IL (US); John Salituro, Union Grove, WI (US); Brian Erickson, Kenosha, WI (US)

(73) Assignee: Abbott Molecular Inc., Des Plaines, IL (US)

( * ) Notice: Subject to any disclaimer, the term of this patent is extended or adjusted under 35 U.S.C. 154(b) by 189 days.

(21) Appl. No.: 14/795,155

(22) Filed: Jul. 9, 2015

(65) Prior Publication Data

US 2016/0053334 A1     Feb. 25, 2016

Related U.S. Application Data

(60) Provisional application No. 62/023,458, filed on Jul. 11, 2014.

(51) Int. Cl.
| | |
|---|---|
| *C12Q 1/68* | (2018.01) |
| *C12P 19/34* | (2006.01) |
| *C12Q 1/70* | (2006.01) |
| *C12Q 1/686* | (2018.01) |
| *C12Q 1/6806* | (2018.01) |
| *G01N 35/00* | (2006.01) |
| *G01N 35/10* | (2006.01) |

(52) U.S. Cl.
CPC ............. *C12Q 1/703* (2013.01); *C12Q 1/686* (2013.01); *C12Q 1/6806* (2013.01); *G01N 2035/00366* (2013.01); *G01N 2035/1032* (2013.01)

(58) Field of Classification Search
None
See application file for complete search history.

(56) References Cited

U.S. PATENT DOCUMENTS

| | | |
|---|---|---|
| 5,284,940 A | 2/1994 | Lin et al. |
| 6,936,414 B2 | 8/2005 | Gundling |
| 2002/0022261 A1 | 2/2002 | Anderson et al. |
| 2006/0183107 A1 | 8/2006 | Melkonyan et al. |
| 2009/0305227 A1 | 12/2009 | Dougherty et al. |
| 2010/0291666 A1 | 11/2010 | Collier et al. |
| 2011/0151430 A1 | 6/2011 | Kowalik et al. |
| 2013/0143205 A1 | 6/2013 | Montagnier |
| 2014/0038172 A1 | 2/2014 | De La Rosa et al. |
| 2015/0292993 A1* | 10/2015 | Huang ................. G01N 33/487 435/6.12 |

OTHER PUBLICATIONS

Olsvik et al., "Evaluation of potential reference genes in real-time RT-PCR studies of Atlantic salmon," BMC Molecular Biology, Nov. 2005, vol. 6, No. 21, pp. 1-9.*
Abbott RealTime HIV-1 PMA, May 2007, pp. 2-29 [retrieved on-line: https://www.fda.gov/downloads/biologicsbloodvaccines/.../ucm091196.pdf; retrieval date Apr. 24, 2017].*
Lofgren et al., "Evaluation of a dried blood spot HIV-1 RNA program for early diagnosis and viral load monitoring at rural and remote health care facilities," AIDS, Nov. 2009, vol. 23, No. 18, pp. 1-15 (print out).*
Scott et al., "Evaluation of Abbott m2000 RealTime Human Immunodeficiency Virus Type 1 (HIV-1) Assay for HIV Load Monitoring in South Africa Compared to the Roche Cobas AmpliPrep-Cobas Amplicor, Roche Cobas AmpliPrep-Cobas TaqMan HIV-1, and BioMerieux NucliSENS EasyQ HIV-1Assay," J. Clin. Microbiology, Jul. 2009, vol. 47, pp. 2209-2217.*
Abbott RealTime HCV Genotype II, publicly available Jun., pp. 1-30 [retrieved on-line Feb. 3, 2018; retrieved from: https://www.accessdata.fda.gov/cdrh_docs/pdf12/P120012c.pdf] (Year: 2013).*
Kleshik, et al. "Analytical performance of an automated assay quantifying HIV-1 from dried blood spots" Journal of Clinical Virology; 2013; vol. 57; pp. 271-273.
McNulty, et al. "Evaluation of dried blood spots for human immunodeficiency virus type 1 drug resistance testing" Journal of Clinical Microbiology; Feb. 2007; vol. 45; No. 2; pp. 517-521.
Pirillo, et al. "Quantification of HIV-RNA from dried blood spots using the Siemens Versant HIV-1 RNA (kPCR) assay" Journal of Antimicrobial Chemotherapy; 2011; vol. 66; pp. 2823-2826.
Smit, et al. "Systematic review of the use of dried blood spots for monitoring HIV viral load and for early infant diagnosis" PLOS One; Mar. 2014; vol. 9; Issue 3; e86461; 8 pages.

* cited by examiner

*Primary Examiner* — Young J Kim
(74) *Attorney, Agent, or Firm* — Pierce Atwood LLP; Kevin M. Farrell

(57) ABSTRACT

The present invention provides novel and non-obvious improvements to dried blood spot testing for HIV-1 viral load useful for diagnosis and monitoring treatment progression.

12 Claims, 9 Drawing Sheets

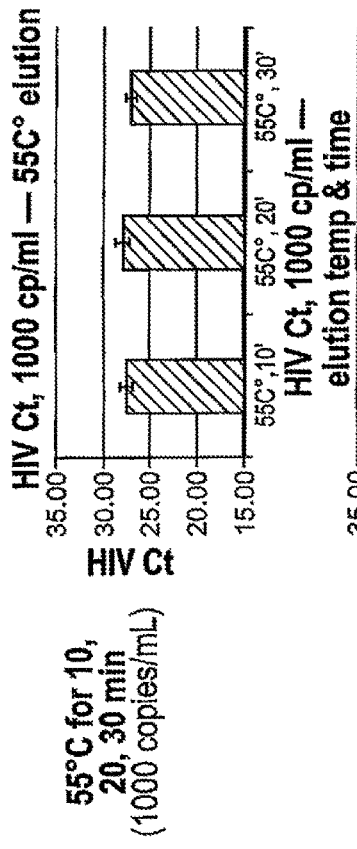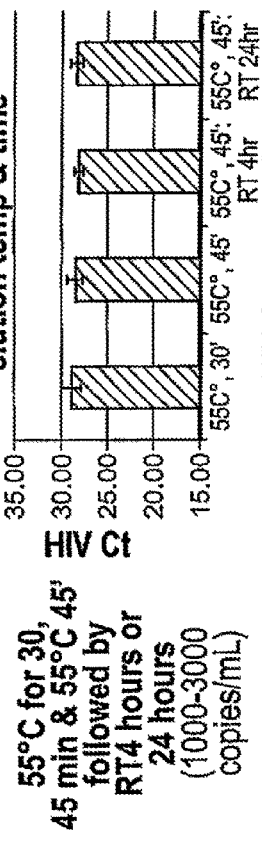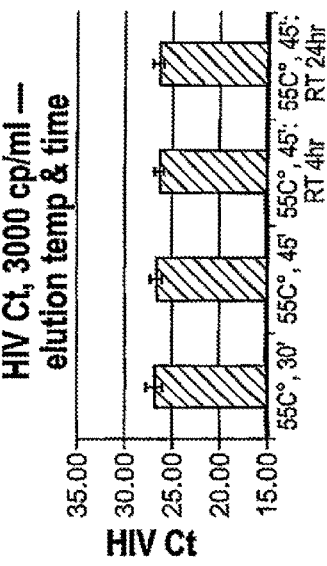
Fig. 7A
Fig. 7B
Fig. 7C

AUTOMATED HIV-1 VIRAL LOAD TESTING PROCEDURE FOR DRIED SPOTS

BACKGROUND

Human Immunodeficiency Virus (HIV) is the etiologic agent of Acquired Immunodeficiency Syndrome (AIDS). (Barre-Sinoussi F, Chermann J C, Rey F, et al. Isolation of a T-lymphotropic retrovirus from a patient at risk for acquired immune deficiency syndrome (AIDS). Science 1983, 220:868-71; Popovic M, Sarngadharan M G, Read E, et al. Detection, isolation and continuous production of cytopathic retroviruses (HTLV-I) from patients with AIDS and pre-AIDS. Science 1984, 224:497-500; Gallo R C, Salahuddin S Z, Popovic M, et al. Frequent detection and isolation of cytopathic retroviruses (HTLV-I) from patients with AIDS and at risk for AIDS. Science 1984, 224:500-3). It can be transmitted through sexual contact, exposure to infected blood or blood products, or from an infected mother to the fetus. (Curran J W, Jaffe H W, Hardy A M, et al. Epidemiology of HIV infection and AIDS in the United States. Science 1988, 239:610-16). Acute HIV syndrome, characterized by flu-like symptoms, develops 3 to 5 weeks after initial infection and is associated with high levels of viremia. (Daar E S, Moudgil T, Meyer R D, Ho D D. Transient high levels of viremia in patients with primary human immunodeficiency virus type 1 infection. New Engl J Med 1991, 324:961-4; Clark S J, Saag M S, Decker W D. High titers of cytopathic virus in plasma of patients with symptomatic primary HIV-1 infection. New Engl J Med 1991, 324:954-60). Within 4 to 6 weeks of the onset of symptoms, HIV specific immune response is detectable. (Albert J, Abrahamsson B, Nagy K, et al. Rapid development of isolate-specific neutralizing antibodies after primary HIV-1 infection and consequent emergence of virus variants which resist neutralization by autologous sera. AIDS 1990, 4:107-12; Horsburgh C R Jr, Ou C Y, Jason J, et al. Duration of human immunodeficiency virus infection before detection of antibody. Lancet 1989, 334:637-40). After seroconversion, viral load in peripheral blood declines and most patients enter an asymptomatic phase that can last for years. (Pantaleo G, Graziosi C, Fauci A S. New concepts in the immunopathogenesis of human immunodeficiency virus (HIV) infection. New Engl J Med 1993, 328:327-35). Quantitative measurement of HIV levels in peripheral blood has greatly contributed to the understanding of the pathogenesis of HIV infection (Ho D D, Neumann A U, Perelson A S, et al. Rapid turnover of plasma virions and CD4 lymphocytes in HIV-1 infection. Nature 1995, 373:123-6; Wei X, Ghosh S K, Taylor M E, et al. Viral dynamics in human immunodeficiency virus type 1 infection. Nature 1995, 373:117-22) and has been shown to be an essential parameter in prognosis and management of HIV infected individuals. (Mellors J W, Rinaldo C R J R, Gupta P, et al. Prognosis in HIV-1 infection predicted by the quantity of virus in plasma. Science 1996, 272:1167-70; Mellors J W, Munoz A, Giorgi J V, et al. Plasma viral load and CD4+ lymphocytes as prognostic markers of HIV-1 infection. Ann Intern Med 1997, 126(12):946-54; Chene G, Sterne J A, May M, et al. Prognostic importance of initial response in HIV-1 infected patients starting potent antiretroviral therapy: analysis of prospective studies. Lancet 2003, 362:679-86; Egger M, May M, Chene G, et al. Prognosis of HIV-1 infected drug patients starting highly active antiretroviral therapy: a collaborative analysis of prospective studies. Lancet 2002, 360:119-29; Wood E, Hogg R S, Yip B, et al. Higher baseline levels of plasma human immunodeficiency virus type 1 RNA are associated with increased mortality after initiation of triple-drug antiretroviral therapy. J Infect Dis 2003, 188:1421-5; US Department of Health and Human Services. 2004 guidelines for the use of antiretroviral agents in HIV-1 infected adults and adolescents. Available online at: AIDSinfo.nih.gov/guidelines). Decisions regarding initiation or changes in antiretroviral therapy are guided by monitoring plasma HIV RNA levels (viral load), CD4+ T cell count, and the patient's clinical condition. (US Department of Health and Human Services. 2004 guidelines for the use of antiretroviral agents in HIV-1 infected adults and adolescents. Available online at: AIDSinfo.nih.gov/guidelines; Yeni P G, Hammer S M, Hirsch M S, et al. Treatment for Adult HIV Infection. 2004 Recommendations of the International AIDS Society-USA Panel. JAMA 2004, 292: 251-65). The goal of antiretroviral therapy is to reduce the HIV virus in plasma to below detectable levels of available viral load tests. (US Department of Health and Human Services. 2004 guidelines for the use of antiretroviral agents in HIV-1 infected adults and adolescents. Available online at: AIDSinfo.nih.gov/guidelines; A S, Essunger P, Cao Y, et al. Decay characteristics of HIV-1 infected compartments during combination therapy. Nature 1997, 387(6629):188-91). HIV RNA levels in plasma can be quantitated by prior art procedures by nucleic acid amplification or signal amplification technologies. (Mulder J, McKinney N, Christopher C, et al. Rapid and simple PCR assay for quantitation of human immunodeficiency virus type 1 RNA in plasma: application to acute retroviral infection. J Clin Microbiol 1994, 32:292-300; Dewar R L, Highbarger H C, Sarmiento M D, et al. Application of branched DNA signal amplification to monitor human immunodeficiency virus type 1 burden in human plasma. J Inf Diseases 1994, 170:1172-9; Van Gemen B, Kievits T, Schukkink R, et al. Quantification of HIV-1 RNA in plasma using NASBA™ during HIV-1 primary infection. J Virol Methods 1993, 43:177-87).

SUMMARY OF THE INVENTION

Quantitative measurement of HIV-1 levels in peripheral blood is an essential parameter to determine disease prognosis and the course of antiretroviral therapy for infected patients. Due to limited viral RNA stability, conventional HIV-1 viral load (VL) testing from plasma imposes restrictive requirements for sample collection, handling and shipment, which can hamper further expansion of VL testing in resource limited settings. Dried spots (DS) including dried blood spots (DBS) represent a feasible option that bypasses these logistic and technical limitations. DS other than DBS can be, for example, plasma, saliva, serum, etc. This invention provides novel and non-obvious methods and procedures of a new HIV-1 DS/DBS VL assay.

The development of DBS assays for the quantification of HIIV-1 RNA and pro-viral DNA (a viral genome, or part thereof, incorporated into the DNA of a host cell) is in its infancy. The assays developed in the art thus far suffer from several disadvantages related to cost and efficiency. For example, many of the current procedures require manual transfer of DS or DBS eluates for further nucleic acid extraction procedures, providing an opportunity for error and contamination to enter in the assay. If DNase treatment is desired or required in the prior art assays, the procedures often involve the use of additional reagents (specific DNase reaction buffers and deactivation buffers), equipment (heating devices), time (for the DNase procedural steps to be completed) and additional manual manipulation.

The procedure of the present invention reduces and eliminates these drawbacks of the prior art. The DS/DBS HIV-1 VL assay of the present invention utilizes a novel workflow and an innovative elution/reaction buffer system. These improvements over the prior art result in an assay that can be almost completely automated with increased accuracy and efficiency over the prior art. Further, these improvements over the prior art permit the use of DNase without the added time and inconvenience inherent in the prior art procedures where DNase is utilized.

The present invention contemplates an automated method for detecting HIV-1 nucleic acids in a blood sample, the method comprising: a) providing: i) a blood sample suspected of being infected with HIV dried on a solid carrier, ii) an elution buffer, iii) an automated, programmable sample preparation instrument, iv) an automated, programmable PCR instrument, v) DNase and vi) PCR reagents suitable for detecting HIV-1 nucleic acids; b) eluting the blood sample from the solid carrier with the elution buffer to create an eluted sample; c) loading the eluted sample into the automated, programmable sample preparation instrument for further nucleic acid extraction and purification to create a processed sample; d) loading the PCR reagents into the automated, programmable PCR instrument; e) initiating an automated program to aliquot the PCR reagents into the processed sample; f) performing PCR on the extracted nucleic acids in the processed sample with the automated, programmable PCR instrument; g) analyzing PCR results generated by the automated, programmable PCR instrument to determine if any samples comprise HIV-1 nucleic acids; h) wherein, said elution buffer comprises approximately 3.5 M GITC, approximately 5% Tween® 20 (trade name for polysorbate 20; also referred to as polyoxyethylene (20) sorbitan monolaurate), approximately 50 mM KOAc (potassium acetate) at approximately pH 6.0; i) wherein, optionally, DNase is added to one or more of the processed sample, the PCR reagents, or the complete PCR reaction after addition of the PCR reagents to the processed sample.

The invention further contemplates that the method additionally comprises negative and positive controls.

The invention further contemplates that step b) is about 20 minutes at room temperature with gentle intermittent mixing or 55 degree C. for 30 minutes with gentle intermittent mixing.

The invention further contemplates that the automated procedure is programmed by software commands.

The invention further contemplates that step i) is performed and said DNase does not require specific DNase reaction buffers, is effective at ambient temperature or temperatures used during PCR cycling stages, effectively degrades DNA within the time period of 30 minutes, does not need to be inactivated after effectively degrading DNA and does not negatively impact the detection of RNA sequences.

The invention further contemplates that the solid carrier is filter paper.

The invention further contemplates that the nucleic acid is RNA.

The invention further contemplates that the nucleic acid is pro-viral DNA.

DETAILED DESCRIPTION OF THE INVENTION

Figure 1A:
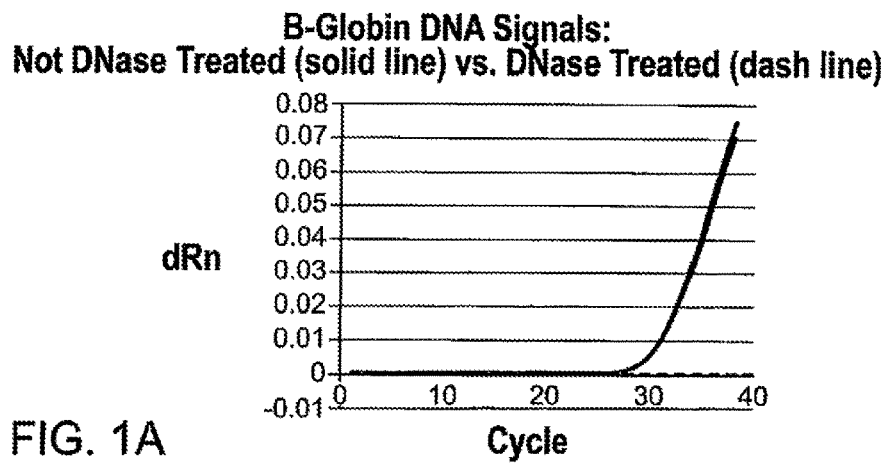
FIG. 1 (A-C) shows DNase (Ambion DNase 1 (RNase-Free) (Cat # AM2222) or equivalent) that effectively removed DNA and did not negatively impact RNA signals. DNase was used to directly treat extracted nucleic acids prior to the performing a PCR reaction. (A) β-globulin DNA signals; (B) HIV DNA signals; (C) internal control (IC) RNA signals.

To date, testing of plasma samples is the gold standard for viral load (VL) evaluation in HIV-infected individuals on antiretroviral therapy (ART). In resource-limited settings, the use of dried blood spots (DBS) is a promising alternative sample type for both VL testing and genotyping. DBS in combination with automated sample processing and real-time PCR-based systems would allow VL measurement or genotyping tests in central laboratories.

To adapt HIV viral load assays to DBS, the most important technical issues are assay sensitivity and specificity. The clinical sensitivity and specificity of the DBS viral load assay are defined by using a threshold of 1000 copies/mL in the World Health Organization (WHO) 2013 guidelines for Anti-Retroviral Treatment. The proportion of patients with plasma VL<1000 copies/mL 12 months or longer after ART initiation is a key outcome measured as part of acquired drug resistance surveys. Patients with VL below this level are categorized as having successful drug therapy (Parkin, 2014 AIDS Rev.)

The assay specificity is related to isolation/amplification of cell-free RNA vs. cell-associated DNA or RNA. If an assay picks up both cell-free RNA and cell-associated DNA or RNA, a significant over-quantification at low plasma VL concentrations will be observed, since cellular DNA is the predominant source of non-plasma virus-derived nucleic acid in dried blood spots. (Parkin, 2014 AIDS Rev.). The Abbott RealTime HIV-1 m2000 system incorporates reagents and methods that are specific or at least selective for RNA (Parkin, 2014 AIDS Rev.). Reports also claim acceptable correlation between viral loads in plasma and DBS samples using the Abbott RealTime HIV-1 assay (Marconi, A., et al., 2009 Clin Microbiol Infect; Arredondo et al., 2012 J Clin Micro).

Assay sensitivity is normally represented by the assay limit of detection (LOD). The main challenge for DBS sensitivity is that volume limitations restrict input copy numbers (review by Nell T. Parkin, 2014). A modified version of the Abbott RealTime HIV-1 DBS assay (Abbott RealTime HIV-1 DBS assay open mode) was developed that involves the use of one perforated 70 µl DBS spot that does not require excision. Additionally, no sample transfer between tubes is required. A DBS is eluted in 1300 µl of buffer with 1000 µl used as input for processing. Therefore, the actual amount of whole blood that is transferred for extraction is approximately 53.8 µl. An experimentally-determined DBS elution recovery rate (compared to plasma) using the current room temperature elution condition (outlined in the initial DBS open mode protocol) ranged from 24% to 43% (compared to plasma), with an average of 35%, which leads to a calculated LOD range of 1080 copies/mL to 1934 copies/mL. (In these experiments, both whole blood and plasma were spiked with the same concentration of HIV; the hematocrit effect was not included). Since the WHO proposed threshold for determining successful ART therapy is a VL of ≤1000 copies/mL (WHO Technical and Operational Considerations for Implementing HIV Viral Load Testing July 2014), the HIV DBS VL assay needs to have a Limit of Detection (LOD)≤1000 copies/mL. To achieve this sensitivity using one 70 µL DBS the DBS elution efficiency needs to be improved by 10% or more to lower the LOD to less than 1000 cp/mL.

The DS/DBS HIV-1 VL assay of the present invention is designed to be run on an automated device that can be programmed for the nucleic acid extraction and amplification parameters of the present invention. The Abbott RealTime m2000sp and m2000rt instruments (device; Abbott Molecular, Abbott Park, Ill.) are examples of suitable automated and programmable devices for the DBS HIV-1 VL assay of the present invention. Operating instructions/parameters for the Abbott Realtime m2000sp and m2000rt instruments (and suitable instruments available from other sources) are known to one of ordinary skill in the art and are incorporated herein by reference. The present invention is not limited to the use of this device and other similar devices were known to those of ordinary skill in the art at the time of this invention. HIV-1 assay of the present invention preferably uses Polymerase Chain Reaction (PCR) technology with homogenous real-time fluorescent detection. Partially double-stranded fluorescent probe design allows detection of diverse HIV-1 variants including groups M, O and N. The assay can be standardized against a viral standard from the Virology Quality Assurance (VQA) Laboratory of the AIDS Clinical Trial Group or other standard (Yen-Lieberman B, Brambilla D, Jackson B, et al. Evaluation of a quality assurance program for quantitation of human immunodeficiency virus type 1 RNA in plasma by the AIDS clinical trials group virology laboratories, *J Clin Microbiol,* 1996, 34:2695-701), and against World Health Organization WHO) International Standards for HIV-1 RNA (NIBSC; Holmes H, Davis C, Heath A, et al. An international collaborative study to establish the 1st international standard for HIV-1 RNA for use in nucleic acid-based techniques, *J Virol Methods,* 2001, 92:141-50; Davis C, Heath A, Best S, et al. Calibration of HIV-1 working reagents for nucleic acid amplification techniques against the 1st international standard for HIV-1 RNA, *J Virol Meth,* 2003, 107:37-44). The assay results can be reported in copies/mL, Log copies/mL, International Units/mL (IU/mL) or Log IU/mL.

As indicated in the WHO Early Infant Diagnosis of HIV—Global HIV Web Study (depts.washington.edu/ghivaids/reslimited/case7/discussion.html), dried-blood spot testing is an acceptable means for collecting samples for analysis and poses a smaller biohazard risk than liquid samples. Further, peer reviewed articles have shown that the use of DBS samples is feasible when compared to plasma samples for sensitivity and reliability (J. Clin Microbiol, 2011, 50(3):569-572).

The efficacy, efficiency and accuracy of automated sample preparation and analysis systems such as the Abbott Sample Preparation System (m2000sp) and Abbott Real-Time PCR analyzer (m2000rt) has been confirmed in peer reviewed journal articles (Marconi, et al., Evaluation of the Abbott Real-Time HIV-1 quantitative assay with dried blood spot specimens, Clin. Microbiol. Infect, 2009, 15:93-97). Further still, comparisons of various papers for the collection of DBS have been published (Rottinghaus, et al., J. Clin. Microbiol., 2012, 51(1):55-60).

Although large amounts of work have investigated the use of DBS in automated preparation and assay systems, improvements in workflow and reagent chemistry are still necessary to provide for increased usability and increased sensitivity. The present invention provides improved efficiency, workflow and performance over prior art DBS HIV-1 VL assay procedures using automated systems.

Advantages of DBS Sample Collection

The advantages of DBS collection over liquid blood samples are numerous. DBS are easy to collect; only a finger prick or heal prick is necessary, bypassing the need for venipuncture. No phlebotomy skills are necessary. Collection equipment is minimal. Sample cards usually have an indication of spot size (diameter) to ensure adequate sample size. A sample volume of about 70 µl is usually adequate. Samples are air dried at ambient conditions. DBS need no refrigeration for storage. DBS can be stored or transported in a closed container (such as Tupper Wear® or a sealed envelope). Samples are easy to transport and are stable for long periods of time at ambient conditions (weeks to months). Thus, samples can be collected at external sites and transported to a centralized testing facility. Because of the lower biohazard afforded with DS/DBS samples, properly packaged samples can be mailed to a test facility (Shipping Guidelines for Dried-Blood Spot Specimens, CDC, www.cdc.gov/labstandards/pdf/nsqap/Bloodspot_Transportation_Guidelines.pdf, and references contained therein; Clinical Laboratory and Standards Institute. Blood collection on filter paper for newborn screening programs; Approved standard—Fifth edition. CLSI document LA4-A6. Wayne, Pa.: Clinical and Laboratory Standards Institute; 2012). Once at the testing facility samples can be extracted using either automated systems or manual procedures if desired.

Definitions

The following definitions are relevant to the present disclosure:

The term "about" or "approximately," unless otherwise stated, refers to a +/−10% variation from the stated value. It is to be understood that such a variation is always included in any given value provided herein, whether or not specific reference is made to it. Further, all recited ranges include all values found within that range whether or not the specific value is actually recited. Thus, the range of 1-10 includes, for example, the values 2, 3.6, 9.015, etc.

The term "polymerase chain reaction (PCR)" refers to a method of making copies of a DNA sequence. The method employs thermal cycling (i.e., cycles of heating and cooling for denaturation (or melting) and replication of the DNA, respectively). Primers, which are short DNA fragments containing sequences complementary to the DNA sequence to be copied, and a heat-stable DNA polymerase, such as the one from *Thermus aquaticus*, which is referred to as Taq polymerase, are used to select the DNA sequence and copy it (see, e.g., U.S. Pat. Nos. 4,683,195; 4,800,195, and 4,965,188, all of which are incorporated by reference herein for their teachings regarding same). With repeated cycling the copies, which are made, are used as templates for generating further copies (i.e., a chain reaction). PCR techniques include, but are not limited to, standard PCR, allele-specific PCR, assembly PCR, asymmetric PCR, digital PCR, Hot-start PCR, intersequence-specific PCR, inverse PCR, ligation-mediated PCR, methylation-specific PCR, mini-primer PCR, nested PCR, overlap-extension PCR, real-time PCR, reverse transcription-PCR, solid phase PCR, thermal asymmetric interlaced PCR, and Touchdown PCR.

The term reverse transcription polymerase chain reaction (RT-PCR) refers to a method of qualitatively detecting gene expression through the creation of complementary DNA (cDNA) transcripts from RNA.

The term "real-time polymerase chain reaction," "real-time PCR" and qualitative PCR" (qPCR) refer to a method of quantitatively measuring the amplification of DNA using fluorescent probes.

The term "primer" as used herein refers to an oligonucleotide that initiates template-dependent nucleic acid synthesis. In the presence of a nucleic acid template, nucleoside triphosphate precursors, a polymerase, and cofactors, under suitable conditions of temperature and pH, the primer can be extended at its 3' terminus by the addition of nucleotides by the polymerase to yield a primer extension product. The primer may vary in length depending on the particular conditions employed and the purpose of the amplification. For example, a primer for amplification for a diagnostic purpose is typically from about 15 to about 35 nucleotides in length. The primer must be of sufficient complementarity to the desired template to prime the synthesis of the desired extension product. In other words, the primer must be able to anneal with the desired template strand in a manner sufficient to provide the 3' hydroxyl moiety of the primer in appropriate juxtaposition for use in the initiation of synthesis by a polymerase. It is not necessary for the primer to be an exact complement of the desired template. For example, a non-complementary nucleotide sequence can be present at the 5' end of an otherwise complementary primer. Alternatively, non-complementary bases can be interspersed within the oligonucleotide primer, provided that the primer sequence has sufficient complementarity with the sequence of the desired template strand to provide a template-primer complex for the synthesis of the extension product.

PCR

Target sequences are amplified with techniques known in the art. The technique of choice is polymerase chain reaction (PCR). PCR amplification can be performed by standard PCR techniques, following a manufacturer's instructions. The Abbott m2000 system comprises devices that automate sample preparation and PCR reactions based on input from the user.

The amplification reaction can, and preferably does, comprise an internal control (IC) nucleic acid and a pair of primers for amplifying the IC nucleic acid. When the amplification reaction comprises an IC nucleic acid, the conditions that promote amplification also promote amplification of the IC nucleic acid. Any suitable sequence can be used as the IC. Examples of IC target sequences include those used in the Exemplification section, below.

Although any suitable sample of a tissue or a body fluid can be used as the source of the sample of nucleic acid, i.e., DNA or RNA, in the present invention the sample is eluted from a DBS. A proteinase, such as proteinase K, can be added to the sample to digest unwanted proteins, if necessary or desired.

The sample may be prepared for assay using any suitable method as is known in the art. Desirably, the method extracts and concentrates nucleic acids. The method also desirably makes the target sequence accessible for amplification, and removes potential inhibitors of amplification from the extract. In the present invention, nucleic acids are eluted from the DBS with the elution buffer of the present invention.

Once the sample is eluted, RNA can be isolated, reverse-transcribed and the resulting cDNA can be amplified (e.g., reverse-transcription polymerase chain reaction (RT-PCR) as described in U.S. Pat. Nos. 5,310,652; 5,322,770; 5,561,058; 5,641,864; and 5,693,517, for example). Further, DNA can be amplified directly without the use of a reverse transcriptase. Pro-viral DNA can be amplified in this way.

The target nucleic acid can be contacted with primers that result in specific amplification of a target sequence, if the target sequence is present in the sample. "Specific amplification" means that the primers amplify a specific target sequence and not other sequences. See, e.g., PCR Technology: Principles and Applications for DNA Amplification (Erlich, Editor, Freeman Press, NY (1992)); PCR Protocols: A Guide to Methods and Applications (Innis, et al., Editors, Academic Press, San Diego, Calif. (1990)); Current Protocols in Molecular Biology (Ausubel, 1994-1999, including supplemental updates through April 2004); and Molecular Cloning: A Laboratory Manual (Sambrook & Russell, 3rd ed., 2001) as well as the methods are described in Intl Pat. App. Pub. No. WO 93/22456 and U.S. Pat. Nos. 4,851,331; 5,137,806; 5,595,890; and 5,639,611, all of which are specifically incorporated herein by reference for their teachings regarding same.

A primer can be detectably labeled with a label that can be detected by spectroscopic, photochemical, biochemical, immunochemical or chemical means, for example (see, e.g., Sambrook, et al.). Useful labels include a dye, such as a fluorescent dye, a radioactive label, such as $^{32}P$, an electron-dense reagent, an enzyme, such as peroxidase or alkaline phosphatase, biotin, or haptens and proteins for which antisera or monoclonal antibodies are available. In the present invention fluorescent dyes are preferred. In this regard, a detectable oligonucleotide can be labeled, such as with fluorescein. If the primer is labeled with a dye and the detectable oligonucleotide is labeled with fluorescein and is designed to bind to the nascent strand opposite from the dye, fluorescence resonance energy transfer (FRET) across the DNA helix can occur. Other detectable oligonucleotides include a molecular probe, a TAQMAN® probe, a single-stranded DNA probe, a double-stranded DNA probe, and the like.

Nucleic acid amplification reagents (PCR reagents) include an enzyme having polymerase activity (e.g., Ampli-Taq Gold®), one or more enzyme co-factors (e.g., $MgCl_2$), and deoxynucleotide triphosphates (dNTPs; e.g., dATP, dGTP, dCTP, and dUTP or dTTP).

Conditions that promote amplification are those that promote annealing of primers and extension of nucleic acid sequences. Annealing is dependent on various parameters, such as temperature, ionic strength, length of sequences being amplified, complementarity, and G:C content of the sequences being amplified. For example, lowering the temperature promotes annealing of complementary nucleic acid sequences. High G:C content and longer length stabilize duplex formation. Generally, primers and detectable oligonucleotides of about 30 bp or less and having a high G:C content work well. Preferred amplification conditions, primers and detectable oligonucleotides are exemplified herein.

Amplification can be repeated for any suitable number of times by thermal cycling the reaction mixture between about 10 and about 100 times, such as between about 20 and about 75 times, such as between about 25 and about 50 times.

Once the amplification reactions are completed, the presence of an amplified product can be detected using any suitable method. Such methods include, without limitation, those known in the art, such as gel electrophoresis with or without a fluorescent dye (depending on whether the product was amplified with a dye-labeled primer), a melting profile with an intercalating dye (see, e.g., PCR Technology, Principles, and Applications for DNA Amplification, Erlich, Ed., W. H. Freeman and Co., New York, 1992, Chapter 7), and hybridization with an internal detectable oligonucleotide. Other examples of methods include enzyme-linked immunosorbent assay (ELISA), electro-chemiluminescence, reverse dot blots, high pressure liquid chromatography (HPLC) (see, e.g., Lazar, Genome Res. 4: S1-S14 (1994)), and single-strand conformation polymorphism analysis of single-stranded PCR products also can be used (see, e.g., Orita, et al., PNAS USA 86: 2766-2770 (1989)). In the present invention fluorescent labels are detected automatically with the automated PCR reaction device.

Amplified nucleic acid can be detected by monitoring an increase in the total amount of double-stranded DNA (dsDNA) in the reaction mixture (see, e.g., U.S. Pat. No. 5,994,056 and European Pat. Pub. Nos. 487,218 and 512, 334). A DNA-binding dye, such as SYBR Green, is used. The dye fluoresces when bound to dsDNA, and the increase in fluorescence is used to determine the increase in dsDNA.

Alternatively and preferably, the amplification and detection can be combined in a real-time PCR assay. When real-time PCR is used, the mixture can further comprise nucleic acid detection reagents. Examples include non-specific fluorescent dyes that intercalates with any double-stranded DNA or a sequence-specific DNA detectable oligonucleotides which permits detection only after the detectable oligonucleotide hybridizes with its complementary DNA target, thereby enabling simultaneous amplification and detection. When a detectable oligonucleotide is present in the mixture during amplification, the detectable oligonucleotide should be stable under the conditions that promote amplification, should not interfere with amplification, should bind to its target sequence under amplification conditions, and emit a signal only upon binding its target sequence. Examples of detectable oligonucleotide that are particularly well-suited in this regard include molecular beacon detectable oligonucleotides, TAQMAN® detectable oligonucleotides, and linear detectable oligonucleotides, such as those described by Abravaya, et al. (U.S. Pat. App. Pub. No. 2005/0227257). The detectable oligonucleotides can form the loop and stem arrangement in combination with a molecular beacon. The detectable oligonucleotides also can be used as linear detectable oligonucleotides with a fluorophore (e.g., FAM) at one end and a high-efficiency quencher, such as the Black Hole Quencher (BHQ®; Bio-Search Technologies, Inc., Novato, Calif.), at the other end.

The terms and expressions, which have been employed, are used as terms of description and not of limitation. In this regard, where certain terms are defined, described, or discussed herein, all such definitions, descriptions, and discussions are intended to be attributed to such terms. There also is no intention in the use of such terms and expressions of excluding any equivalents of the features shown and described or portions thereof.

It is recognized that various modifications are possible within the scope of the claimed invention. Thus, it should be understood that, although the present invention has been specifically disclosed in the context of preferred embodiments and optional features, those skilled in the art may resort to modifications and variations of the concepts disclosed herein. Such modifications and variations are considered to be within the scope of the invention as defined by the appended claims.

All patents, patent application publications, journal articles, textbooks, and other publications mentioned in the specification are indicative of the level of skill of those in the art to which the disclosure pertains. All such publications are incorporated herein by reference to the same extent as if each individual publication were specifically and individually indicated to be incorporated by reference.

The invention illustratively described herein may be suitably practiced in the absence of any element(s) or limitation(s), which is/are not specifically disclosed herein. Thus, for example, each instance herein of any of the terms "comprising," "consisting essentially of," and "consisting of" may be replaced with either of the other two terms. Likewise, the singular forms "a," "an," and "the" include plural references unless the context clearly dictates otherwise. Thus, for example, references to "the method" includes one or more methods and/or steps of the type, which are described herein and/or which will become apparent to those ordinarily skilled in the art upon reading the disclosure.

EXEMPLIFICATION

Example 1

The present invention is preferably performed on automated, programmable PCR devices, several of which are known to one of ordinary skill in the art and are suitable for use with the present invention with any procedural changes that may be necessary for use with a specific system, while not deviating from the inventive concepts of the present invention. In other instances, the present invention may be performed manually. However, manual execution of the present invention results in increased time investment and possible decrease in accuracy due to operator error.

This exemplification utilizes the Abbott m2000 system comprising the m2000sp (sample preparation) and m2000rt (real-time nucleic acid amplification) instruments and the Abbott RealTime HIV-1 reagents.

HIV-1 Viral Load Testing of Dried Blood Spot Specimens for Use in Conjunction with Abbott m2000 Instruments (or Similar) and Abbott RealTime HIV-1 Reagents (or Similar)

The procedure described below applies to HIV-1 viral load testing of dried blood spot (DBS) specimens. This procedure described below is used in conjunction with the Abbott m2000sp and m2000rt instruments and the Abbott RealTime HIV-1 reagents. Other systems and devices are available in the art and one of ordinary skill in the art can modify the below disclosed procedure for use in the other available systems and devices based on the teachings of the present specification and without deviating from the inventive concepts of the present specification.

Instrument Procedure

The application file (i.e., software) for HIV-1 DBS viral load testing must be installed on the Abbott m2000sp and Abbott m2000rt systems prior to performing the assay.

Specimen Collection and Handling Instructions

DBS may be made on a Munktell TFN (Sweden) paper card (or equivalent paper cards, as are known to those of ordinary skill in the art) by following these steps:

Spot whole blood onto the one-half-inch (12-millimeter) circles on a Munktell TFN paper card (or equivalent), ensuring that the entire circle is covered. It is recommended that at least 70 µl blood (~3-5 drops; do not squeeze or milk finger) be used for each circle to ensure full coverage. If whole blood has been collected in a blood collection tube, the freshly drawn blood may be held from 2-8° C. (refrigerator temperature) to 15-30° C. (ambient temperature) for up to 24 hours before spotting. In addition, the blood should be mixed prior to spotting using a pipette.

Air dry the card at ambient temperature.

For transport or storage, package each card in a bag or other sealable container with desiccant packs. The cards may be stored under ambient conditions for up to 12 weeks. Alternatively, cards may be stored at 2-8° C. or −10° C. or colder for up to 24 weeks.

Ship specimens, if necessary or desired, according to the recommended storage temperature and times listed above. For domestic and international shipments, specimens should be packaged and labeled in compliance with applicable state, federal, and international regulations covering the transport of clinical, diagnostic, or biological specimens.

Assay Protocol

1. This exemplary protocol used the Abbott RealTime system. One of ordinary skill in the art will be able to adapt this protocol to other similar devices and systems without undue experimentation. A total of 96 samples can be processed in each run. A negative control, a low positive control, and a high positive control are included in each run, therefore allowing a maximum of 93 DBS specimens to be processed per run when calibrators are not included. These steps do not apply to Abbott controls and calibrators, which should be processed as directly liquid samples. Process the DBS specimens by following these steps:

Prepare Abbott Transport Tubes with 1.3 ml DS/DBS elution buffer (elution buffer comprises approximately 3.5 M GITC (guanidinium thiocyanate), approximately 5% Tween® 20, approximately 50 mM KOAc (potassium acetate) at approximately pH 6.0). Tween® is a registered trademark of ICI Americas, Inc., Bridgewater, N.J. Tween® 20 is a trade name for polysorbate 20. Other brands of polysorbate 20 will also work in the methods of the present invention. [GITC may be used from 1.0-5.5 M, 2.0-4.5 M, 3.0-4.0 M and about 3.5 M; Tween20 may be used at 0-20%, 2%-8%, 4%-6% and about 5%; Potassium Acetate may be used at 10-500 mM, 20 mM-300 mM, 30 mM-200 mM, 40 mM-100 mM and about 50 mM; and pH may be from 5-10, 5.2-8, 5.6-7, 5.8-6.5 and about 6.5.]

Separate one (1) entire DBS for each specimen from a Munktell TFN paper card (or equivalent). Each DBS should be approximately one-half-inch (12 millimeters) in diameter. NOTE: If applicable, avoid direct contact of the cutting surface with DBS specimens. Clean the instrument used to cut DBS between specimens, if necessary, according to good laboratory practices. Place DBS in the Abbott Transport Tube containing the DS/DBS elution buffer. Ensure that the DBS is fully submerged in the DS/DBS elution buffer. NOTE: During this DBS transfer step, a perforated Munktell TFN paper card may be placed above the Abbott Transport Tube where DBS is pushed out of the card and further directly into the tube using a clean pipette tip.

Incubate at room temperature for about 20 minutes or incubate for 30 minutes at 55° C. with intermittent gentle mixing prior to sample being placed on the Abbott m2000sp instrument or other robotic system (Step 7).

2. Thaw appropriate assay controls and internal control (IC) at 15 to 30° C. or at 2 to 8° C. (and between). Thaw calibrators at 15 to 30° C. or at 2 to 8° C. (and between) only if performing a calibration run.

Once thawed, assay controls, IC, and calibrators can be stored at 2 to 8° C. for up to 24 hours before use.

Vortex (i.e., mix extremely vigorously for example with a Vortex mixer or equivalent) each assay calibrator and each control 3 times for 2 to 3 seconds before use. Ensure that the contents of each vial are at the bottom after vortexing by tapping the vials on the bench to bring liquid to the bottom of the vial. Ensure bubbles or foam are not generated; and if present, remove the bubbles with a sterile pipette tip, using a new tip for each vial.

Prepare internal controls (IC) as per manufacturer's instructions, as known in the art.

3. Thaw amplification reagents at 15 to 30° C. or at 2 to 8° C. (and between) and store at 2 to 8° C. until required for the amplification master mix procedure.

Once thawed, the amplification reagents can be stored at 2-8° C. for up to 24 hours if not used immediately.

Prepare amplification reagents (PCR reagents) as per manufacturer's instructions, as known in the art.

Place the low and high positive controls, the negative control, the calibrators, if applicable, and the DBS specimens in the Abbott Transport Tubes onto the Abbott m2000sp sample racks. NOTE: Ensure that the Abbott m2000sp sample racks have been calibrated specifically for this HIV-1 DBS viral load procedure.

Load the sample racks carefully to avoid splashing. If used, bar codes on tube labels must face to the right for scanning. Ensure that each tube is placed securely in the sample rack so that the bottom of the tube reaches the inside bottom of the rack.

Load filled sample racks onto the Abbott m2000sp in consecutive sample rack positions, with the first rack farthest to the right on the worktable, and any additional rack progressively to the left of the first rack.

5. Place the 5 ml Reaction Vessels into the Abbott m2000sp 1 ml subsystem carrier.

6. Load the Abbott mSample Preparation System reagents and the Abbott 96 Deep-Well Plate on the Abbott m2000sp worktable.

7. From the Protocol screen, select the HIV-1 DBS viral load application file. Initiate the sample extraction protocol.

Enter calibrator (needed if a calibration curve has not been stored on the Abbott m2000rt) and control lot specific values in the Sample Extraction: Worktable Setup, Calibrator and Control fields. Lot-specific values are specified in each Abbott RealTime HIV-1 Calibrator and Control Kit Card.

The Abbott m2000sp Master Mix Addition protocol (step 9) must be initiated within 1 hour after completion of Sample Preparation.

NOTE: Change gloves before handling the amplification reagents.

8. Load the amplification reagents and the master mix vial on the Abbott m2000sp worktable after sample preparation is completed.

9. Select the appropriate deep-well plate that matches the corresponding sample preparation extraction. Initiate the Abbott m2000sp Master Mix Addition protocol.

After sample extraction is complete, the Abbott m2000sp automatically fills any empty wells in the Abbott 96-Well Optical Reaction Plate when there are greater than 48 samples processed within a run. Plate fill is not performed for runs containing 48 samples or fewer.

10. Switch on and initialize the Abbott m2000rt instrument in the Amplification Area.

11. Seal the Abbott 96-Well Optical Reaction Plate after the Abbott m2000sp instrument has completed addition of samples and master mix according to the Abbott m2000sp Operations Manual, Operating Instructions section.

12. Place the sealed optical reaction plate into the Abbott Splash-Free Support Base for transfer to the Abbott m2000rt instrument.

13. Place the Abbott 96-Well Optical Reaction Plate in the Abbott m2000rt instrument. From the Protocol screen, select the HIV-1 DBS viral load application file. Initiate the protocol as described in the Abbott m2000rt Operations Manual, Operating Instructions section.

14. DNase may be added to the one or more of the eluted sample, the PCR reagents and the complete PCR reaction after addition of the PCR reagents to the eluted sample, if deemed necessary by the operator. DNase reaction reagents/buffers and deactivation reagents/buffers are not necessary.

Results

The concentration of viral HIV-1 RNA in a specimen or control is calculated from the stored calibration curve. The Abbott m2000rt instrument automatically reports the results on the Abbott m2000rt workstation. Assay results can be reported in copies/ml, log [copies/ml], International Units (IU)/mL, or log [IU/mL]. For interpretation of results see Table 1, below.

TABLE 1

| INTERPRETATION OF RESULTS | |
| --- | --- |
| Result | Interpretation |
| Not detected | Target not detected |
| <7.00 Log (Copies/mL) | Detected* |
| >7.00 Log (Copies/mL) | >ULQ$^a$ |

$^a$ULQ = upper limit of quantitation

*For the research AppSpec File (v4 or higher), all detected specimens will be reported with a VL result. The actual LOD will be provided after verification study. Once verification LOD value is obtained, "Detected" results will be separated to two categories: 1). "Detected" 2). "Detected, <LOD value".

Example 2

The exemplification shows the design features that enable the automated DBS assay procedure of the present invention to work with improved efficiency and sensitivity over prior art methods.

The procedures involve the following steps:
1. DBS is separated from the DBS card.
2. DBS is incubated in a treatment buffer.
3. Reaction vessel containing the DBS in the buffer is loaded on the automated robotic system (e.g., the Abbott m2000sp).
4. The robotic system is driven by a script to process the DBS sample through the nucleic acid extraction process by directly handling the tube where DBS has been incubated without manual intervention.
5. After the nucleic acid extraction, the robotic system forms the PCR master mix (i.e., the complete PCR reaction without the target nucleic acids). Alternatively, this step may be bypassed if the PCR master mix has been formed a priori and loaded on the system.
6. The robotic system forms the complete PCR reaction by combining the extracted nucleic acids obtained at the end of Step 4 with the PCR master mix obtained at the end of Step 5.
7. PCR cycling and data reduction/result reporting are performed on an analytical instrument (e.g., real-time PCR instrument such as the Abbott m2000rt).
8. If desired by the specific application, DNase is added to and incubated with the extracted nucleic acids obtained from Step 4 to eliminate/reduce DNA content. In such a case, the DNase treated nucleic acids will be further processed starting from Step 6. Alternatively, DNase may be added to the PCR reagents before or during the formation of the PCR master mix. Further alternatively, DNase may be formulated in the PCR reagent(s). In such a case, the DNase-containing PCR master mix will be further processed starting from Step 6. During Step 6, DNase is distributed to each sample by the robotic system, bypassing the manual distribution of DNase. In addition, a DNase treatment incubation may be needed after Step 6 before Step 7.

Note: A specific application where the use of DNase may be desired is HIV RNA specific PCR where the interference from the proviral DNA can be eliminated/reduced.

The technologies that enable the above assay procedures and assay performance include:
1. The treatment buffer that elutes nucleic acid from DS/DBS with high efficiency. This disclosure includes the use of Abbott's mWash 1 buffer (3.5M GITC; 5% Tween 20; 50 mM KOAc, pH 6.0) as the DBS treatment/elution buffer. Note: Abbott has previously provided a commercial HIV DBS VL protocol and a commercial CE-IVD HIV Qualitative DBS assay that use Abbott mLysis buffer as the treatment buffer (4.66M GITC; 10% Tween 20; 100 mM Trizma, pH 7.8). A comparison of these two procedures is provided below and shows the unexpected superiority of the procedure of the present invention.
2. The script parameters that enable the robotic pipette system to transfer the liquid directly from the tube containing solid DBS material for further processing in a robust and accurate way while leaving behind a dead volume of ≤300 ul in the tube after the liquid transfer.
3. The use of DNase that effectively degrades DNA in the extracted nucleic acids without including specific DNase reaction buffers.
4. The use of DNase with the property as described in item 3 that effectively degrades DNA at ambient temperature.
5. The use of DNase with the properties as described in items 3 and 4 that effectively degrades DNA within the time period of 30 minutes.
6. The use of DNase with the properties as described in items 3-5 that does not need to be inactivated with either introduction of reagents or elevated temperatures.
7. The use of DNase that effectively degrades DNA in the PCR reaction when DNase has been introduced to PCR reagents prior to exposure to extracted nucleic acids or is introduced during the formation of the PCR reaction.
8. The use of DNase with the property as described in item 7 without including specific DNase reaction buffer.
9. The use of DNase with the properties as described in items 7 and 8 that effectively degrades DNA at ambient temperature or temperatures during various PCR cycling stages.
10. The use of DNase with the properties as described in items 7-9 that effectively degrades DNA within the time period of 10 minutes. Preferably, in the case where temperatures during various PCR cycling stages can support DNase function, the DNase treatment does not require additional time or cycling stage(s) beyond what are included in the PCR cycling.
11. The use of DNase with properties as described in items 7-10 that does not need to be inactivated with either introduction of reagents or elevated temperatures prior to and during PCR.
12. The use of DNase and associated DNase treatment conditions in items 3-11 that do not negatively impact the detection of RNA sequences.
13. The use of the "PCR volume" setting (as a thermal cycling parameter) to be lower than the actual PCR volume. This setting eliminates the "edge" effect observed in a full PCR plate that negatively impacts the sensitivity when compared with a run in a partial PCR plate. The "edge" effect as seen with some state of the art real-time PCR cyclers is caused by the temperature overshoot by the thermal control unit. The lower PCR volume setting leads to slower and more accurate thermal control, thereby alleviating the majority of the temperature overshoot.
14. The PCR reaction cutoff is determined by one of skill in the art as to what is appropriate for the specific DS/DBS target sample.

Details of an Exemplification of the Technologies of the Present Invention:
1. The robotic transfer of liquid from DBS-containing tubes consists of the following steps:
    The DBS is pushed to the bottom of the sample input tube by a disposable tip using a "Detect Tube Bottom" algorithm.
    The disposable tip is slowly retracted by a small distance (e.g., 3 mm) from the bottom of the sample input tube and a small volume aspiration (e.g., 50 µl) is performed to verify that the DBS is not interfering with the disposable tip. After the small volume aspiration is complete, the disposable tip is retracted to a point above the surface of the liquid.
    Using the same disposable tip, the surface of the liquid is detected and a partial volume tracking aspiration (e.g., 450 µl to achieve 1 mL) is performed from that location. After the first partial volume aspiration is complete, the liquid contained in the disposable tip is transferred to a reaction tube for further nucleic acid extraction steps.
    These steps are repeated to obtain the total sample transfer volume.
2. Exemplary DNases that effectively degrade DNA when used in conjunction with the methods and compositions of the present invention when added to extracted nucleic acids (without negatively impacting RNA detection) in the absence of specific DNase reaction buffers and that do not need to be inactivated with either introduction of reagents or elevated temperatures are:
    Promega (Madison, Wis.) RQ1 RNase-Free DNase (Cat # M6101); 2 U/reaction; Room temperature; 30 minutes.
    Ambion (Grand Island, N.Y.) DNase I (RNase-Free) (Cat # AM2222); 2 U/reaction; Room temperature; 30 minutes.
    Roche (Basel, Switzerland) DNase I recombinant, RNase-free (Cat #04716728001); 20 U/reaction; Room temperature; 30 minutes.
    Other suitable DNases may be known to and can be identified by one of ordinary skill in the art using the methods described herein without undue experimentation. The present invention is not limited to any specific DNase so long as it meets the standards listed in this specification. The assays described in the figures below are exemplary only and do not serve to limit the invention to any particular DNase or any particular method of screening.

Figure 1B:
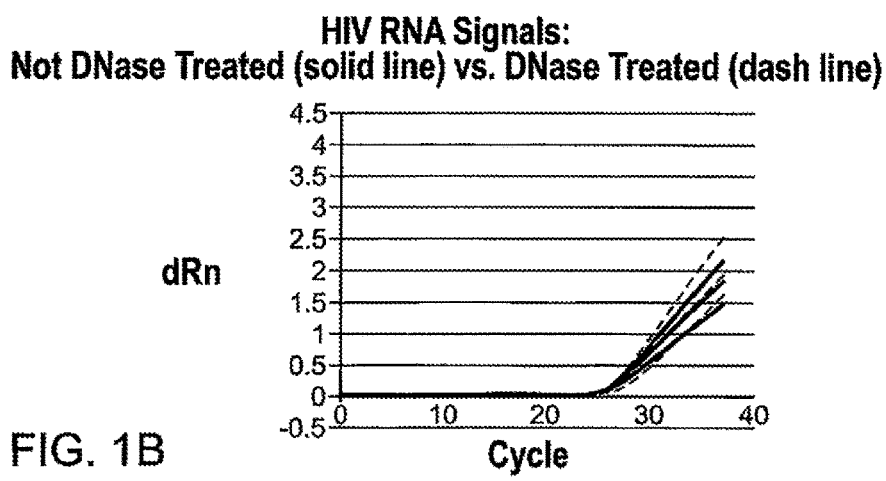
Figure 1C:
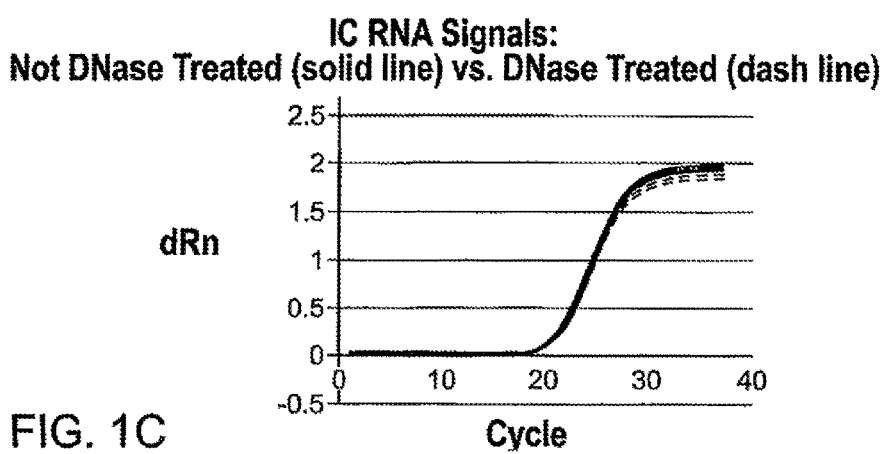

Refer to FIG. 1 for a DNase that effectively removed DNA and did not negatively impact RNA signals. FIG. 1 shows nucleic acid elutes extracted from HIV positive dried blood spots treated with DNase before combined with PCR reagents (dashed lines) in comparison with control (no DNase treatment, solid lines). The nucleic acids were then assayed with a beta globin real-time PCR for the beta globin DNA signal and an HIV-1 real-time RT-PCR for the HIV and IC RNA signals. a) Beta globin DNA signal, to demonstrate effectiveness of DNase treatment, b) HIV RNA signal, to demonstrate the impact of DNase treatment, c) IC RNA signal, to demonstrate the impact of DNase treatment. Conditions used for DNase treatment: Ambion DNase 1 (RNase-Free) (Cat # AM2222); 2 U/reaction; room temperature; 30 minutes.

Figure 2A:
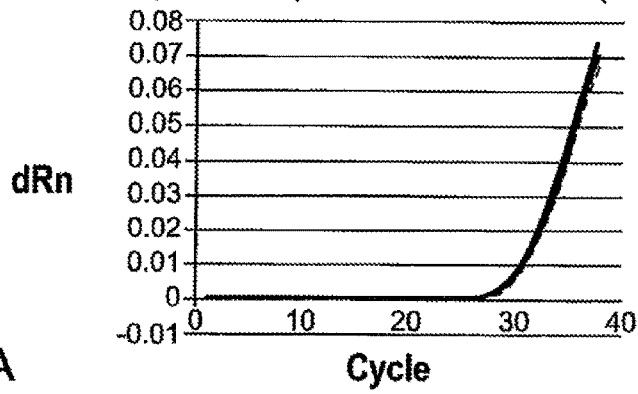
FIG. 2 (A-C) shows DNase (New England Biolabs DNase I (RNase-Free) (Cat # MO303S) or equivalent) that did not effectively remove DNA and did not negatively impact RNA signals. DNase was used to directly treat extracted nucleic acids prior to the performing a PCR reaction. (A) β-globulin DNA signals; (B) HIV DNA signals; (C) internal control (IC) RNA signals.
Figure 2B:
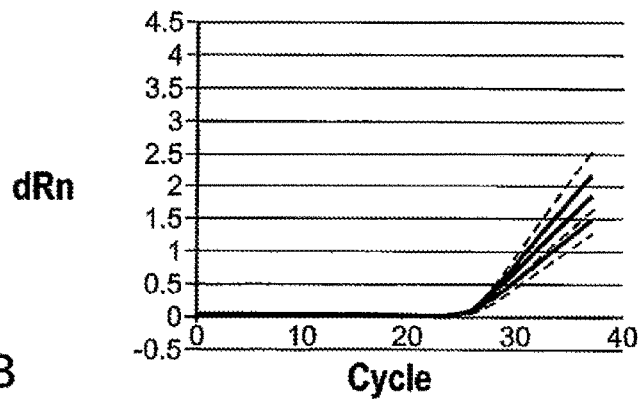
Figure 2C:
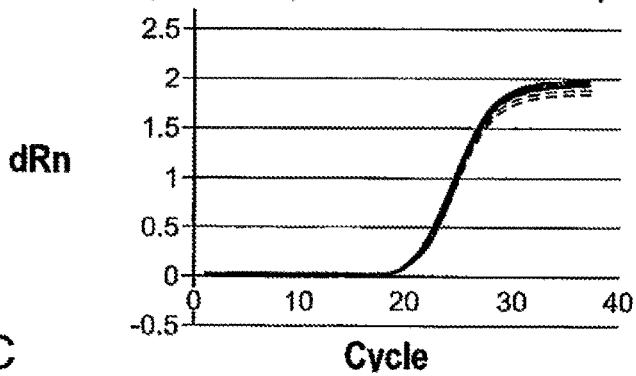

Refer to FIG. 2 for a DNase that did not effectively removed DNA and did not negatively impact RNA signals. FIG. 2 shows nucleic acid elutes extracted from HIV positive dried blood spots treated with DNase before combined with PCR reagents (dashed lines) in comparison with control (no DNase treatment, solid lines). The nucleic acids were then assayed with a beta globin real-time PCR for the beta globin DNA signal and an HIV-1 real-time RT-PCR for the HIV and IC RNA signals. a) Beta globin DNA signal, to demonstrate effectiveness of DNase treatment, b) HIV RNA signal, to demonstrate the impact of DNase treatment, c) IC RNA signal, to demonstrate the impact of DNase treatment. Conditions used for DNase treatment: New England Biolabs DNase I (RNase-Free) (Cat # MO303S); 2 U/reaction; room temperature; 30 minutes.

Figure 3A:
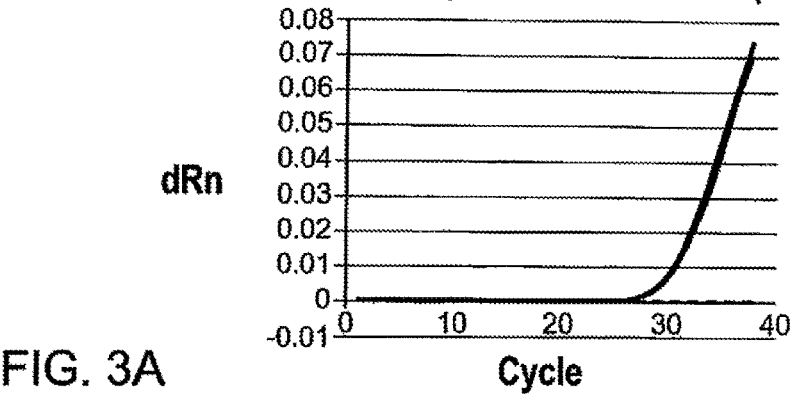
FIG. 3 (A-C) shows DNase (Sigma-Aldrich DNase 1 (Amplification Grade) (Cat # AMPD1) or equivalent) that effectively removed DNA and negatively impacted RNA signals. DNase was used to directly treat extracted nucleic acids prior to the performing a PCR reaction. (A) β-globulin DNA signals; (B) HIV DNA signals; (C) IC RNA signals.
Figure 3B:
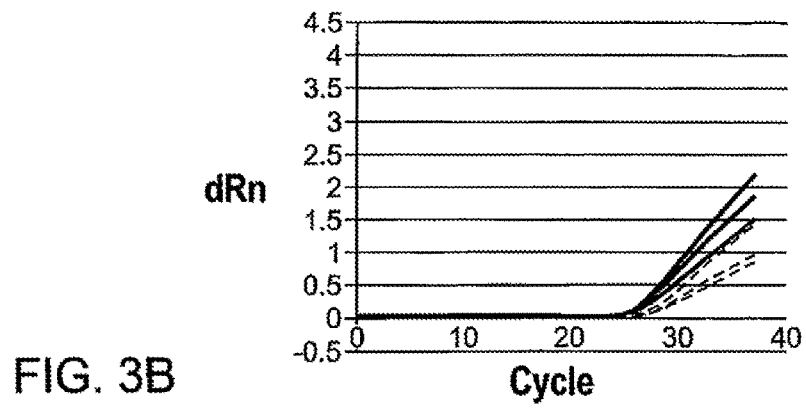
Figure 3C:
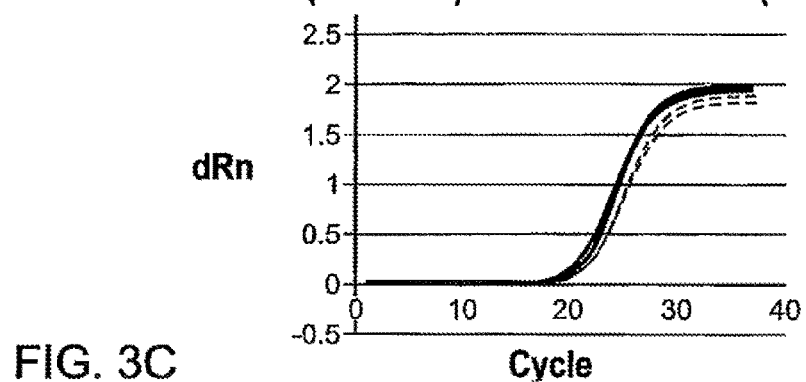

Refer to FIG. 3 for a DNase that effectively removed DNA and negatively impacted RNA signals. FIG. 3 shows nucleic acid elutes extracted from HIV positive dried blood spots treated with DNase before combined with PCR reagents (dashed lines) in comparison with control (no DNase treatment, solid lines). The nucleic acids were then assayed with a beta globin real-time PCR for the beta globin DNA signal and an HIV-1 real-time RT-PCR for the HIV and IC RNA signals. a) Beta globin DNA signal, to demonstrate effectiveness of DNase treatment, b) HIV RNA signal, to demonstrate the impact of DNase treatment, c) IC RNA signal, to demonstrate the impact of DNase treatment. Conditions used for DNase treatment: Sigma-Aldrich DNase 1 (Amplification Grade) (Cat # AMPD1); 2 U/reaction; room temperature; 30 minutes.

Figure 4A:
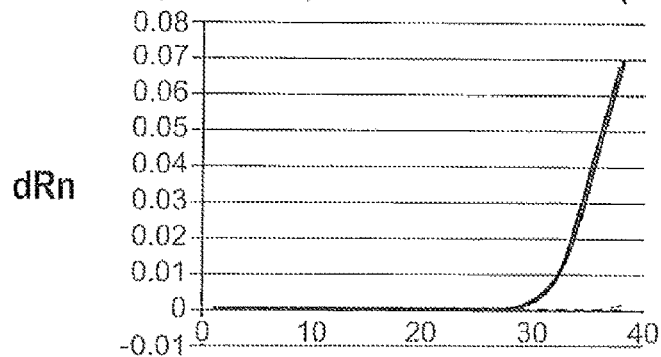
FIG. 4 (A-C) shows DNase (Promega RQ1 RNase-Free DNase (Cat # M6101) or equivalent) that effectively removed DNA and did not negatively impact RNA signals. DNase was used to directly treat extracted nucleic acids prior to the performing a PCR reaction. (A) β-globulin DNA signals; (B) HIV DNA signals; (C) IC RNA signals.
Figure 4B:
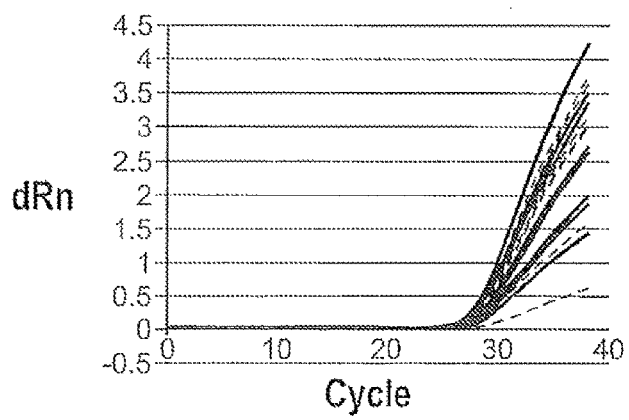
Figure 4C:
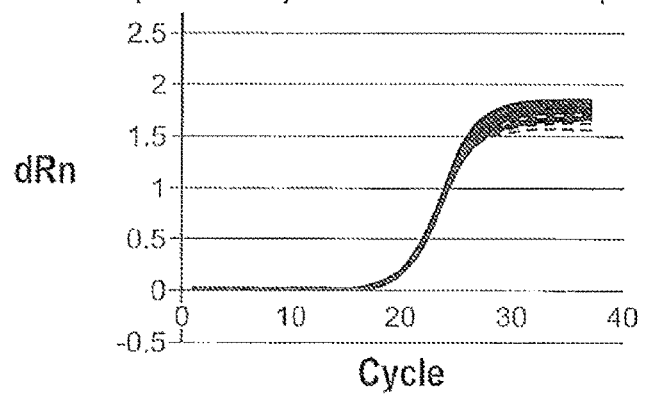

3. Exemplary DNases that effectively degrade DNA in the PCR reaction (without negatively impacting RNA detection) when DNase has been introduced to PCR reagents prior to exposure to extracted nucleic acids or is introduced during the formation of the PCR reaction are:

Promega RQ1 RNase-Free DNase (Cat # M6101); 2 U/reaction; Room temperature; 10 minutes Ambion DNase I (RNase-Free) (Cat # AM2222); 2 U/reaction; Room temperature; 30 minutes Others may be known to one of ordinary skill in the art and could be identified using the methods described herein without undue experimentation. The present invention is not limited to any specific DNase so long as it meets the standards listed in this specification. The assays described in the figures below are exemplary only and do not serve to limit the invention to any particular DNase Refer to FIG. 4 for a DNase that effectively removed DNA and did not negatively impact RNA signals. In FIG. 4, DNase was added to the PCR reagents that were subsequently combined into PCR master mix (dash line). As the control, no DNase was added to the PCR reagents (solid line). The extracted nucleic acids were then assayed by the PCR master mix where beta globin DNA signal, and HIV and IC RNA signals are detected. a) Beta globin DNA signal, to demonstrate effectiveness of DNase treatment, b) HIV RNA signal, to demonstrate the impact of DNase treatment, c) IC RNA signal, to demonstrate the impact of DNase treatment. Conditions used for DNase treatment: Promega RQ1 RNase-Free DNase (Cat # M6101); 2 U/reaction; room temperature; 10 minutes.

Abbott has previously provided a prior art protocol. This protocol was optimized to initial HIV-1 DBS VL open mode (see table below). The initial open mode protocol was further optimized to current open mode and for develop of CE product. Table 2 below shows the differences between the prior art protocol, initial open mode protocol and further improved protocol. The letters "CE" are the abbreviation of French phrase "Conformité Européene" which literally means "European Conformity."

TABLE 2

Differences between the prior art protocol, initial open mode protocol and further improved protocol.

| | Prior Art Protocol | DBS initial open mode optimization | Further optimization for CE product |
|---|---|---|---|
| Number of DBS Per Sample | 2 | 1 | 1 |
| Blood Volume Per DBS | 50 µl | 70 µl | 70 µl |
| DBS Treatment Buffer | 1.7 mL mLysis Buffer (4.66M GITC; 10% Tween 20; 100 mM Trizma, pH 7.8) | 1.3 mL mWash 1 Buffer (3.5M GITC; 5% Tween 20; 50 mM KOAc, pH 6.0) | 1.3 mL mWash 1 Buffer (3.5M GITC; 5% Tween 20; 50 mM KOAc, pH 6.0) |

TABLE 2-continued

Differences between the prior art protocol, initial open mode protocol and further improved protocol.

| | Prior Art Protocol | DBS initial open mode optimization | Further optimization for CE product |
|---|---|---|---|
| Number of Sample Tubes Per DBS | 2 (including a DBS treatment tube and an m2000sp sample input tube) | 1 (m2000sp sample input tube) | 1 (m2000sp sample input tube) |
| Number of Samples Per m2000 Run | 48 | 96 | 96 |
| DBS elution condition | Room temperature 20 minutes with intermittent mix | Room temperature 20 minutes with intermittent mix | 55° C. for 30 minutes |
| Automated DBS Eluate Transfer | No | Yes | Yes |
| DNase Treatment | No | Yes | No |
| Volume of lysis buffer addition at Cell lysis step | 0.8 mL × 3 | 0.8 ml × 3 | 0.8 mL × 2 (to reduce GITC carryover causing 4450/4442 errors) |
| IC addition | 750 µl IC per lysis buffer bottle | 500 µl IC per lysis buffer bottle | 750 µl IC per lysis buffer bottle |
| PCR Parameter | The PCR volume setting (as a thermal cycling parameter) is the same as the actual PCR volume (100 µl) | The PCR volume setting (as a thermal cycling parameter) is lower than the actual PCR volume (25 µl vs. 100 µl) | The PCR volume setting (as a thermal cycling parameter) is lower than the actual PCR volume (25 µl vs. 100 µl) |
| Data Reduction | Higher PCR reactivity Cutoff (MR 0.07) | Lower PCR reactivity Cutoff (MR 0.03) | Lower PCR reactivity Cutoff (MR 0.03) |
| Sensitivity (Target level associated with 95% detection probability) | ~2500 copies/mL | ~1000 copies/mL | ~800 copies/mL |

The changes in the assay as detailed in Table 2 result in a vast, unexpected and surprising improvement over the prior art method. Table 3 shows the increased sensitivity achieved by the method of the present invention. The target level associated with 100% detection decreased from 10,000 copies per ml in the prior art assay to 2,000 copies per ml when using the methods of the present invention.

Table 3 See the table below for the comparison of the open mode protocol (DBS elution condition RT 20 minutes.) invention with the prior art protocol in detection sensitivity.

| | | Prior Art | | Open Mode | |
|---|---|---|---|---|---|
| Target Level (copies/mL) | Number Tested | Number Detected | Percent Detected | Number Detected | Percent Detected |
| 1,000,000 | 12 | 12 | 100 | 12 | 100 |
| 100,000 | 12 | 12 | 100 | 12 | 100 |
| 10,000 | 12 | 12 | 100 | 12 | 100 |
| 3,000 | 12 | 11 | 92 | 12 | 100 |
| 2,000 | 12 | 11 | 92 | 12 | 100 |
| 1,000 | 12 | 7 | 58 | 11 | 92 |
| 500 | 12 | 4 | 33 | 8 | 67 |
| 250 | 12 | 3 | 25 | 8 | 67 |

Example 3

Studies Performed for Sensitivity and Assay Robustness Improvement

With the initial open mode assay, approximately 2-3% internal study samples and >5% external study samples had m2000rt 4450 or 4442 errors and, thus, were invalid. It was determined that residual guanidine led to the increased frequency of inhibition and the 4450 and 4442 errors. The HIV-1 DBS Application Specification File was modified to reduce the amount and frequency of guanidine carryover. Reducing the retraction speed during waste removal reduces the dispersal of any drops hanging from the pipette tips. Since the DBS sample is present in Wash 1 buffer (DBS Elution Buffer) with 1 ml as sample input, the volume of lysis buffer in the reaction could be reduced from 2400 to 1600 µl, reducing the amount of GITC present in each reaction. Washing effectiveness was increased by increasing Wash 2 volume from 700 to 750 µl. Implementing these changes reduced the frequency of 4450 and 4442 errors to approximately 0.2% (Data not shown). This optimization significantly improved assay robustness.

The assay sensitivity can be improved by increasing sample input by using two 70 µL DBS (dried blood spot) per patient for testing. The evaluation data (data not shown) did suggest that at room temperature elution, two DBS compared to one DBS improved the HIV low end detection rate. At the 55° C. 30 minutes elution condition, the improvement in low HIV concentration detection rate of two DBS compared to one DBS was not as distinct.

Figure 5A:
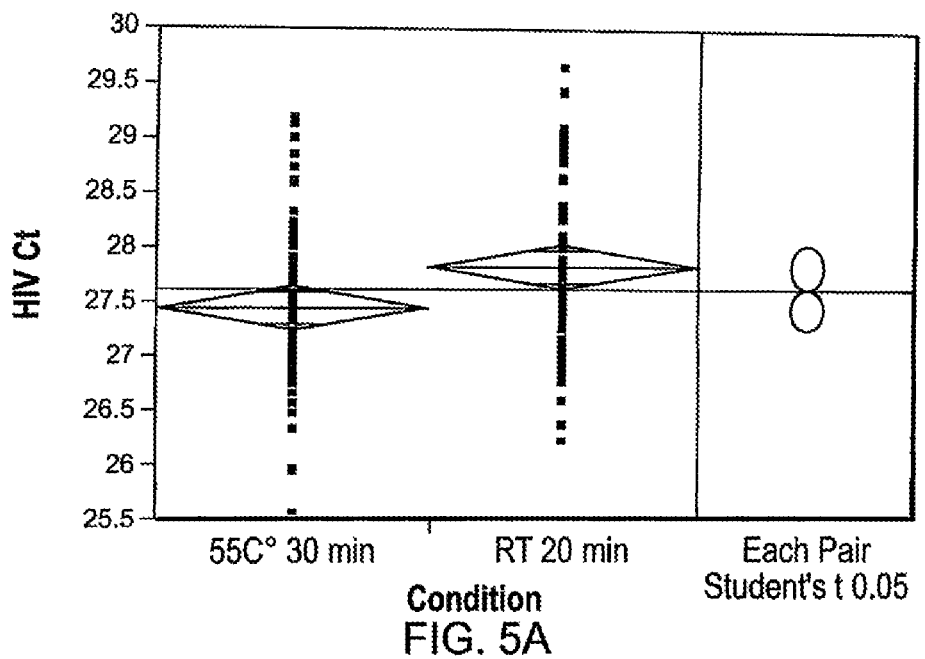
FIGS. 5 (A & B) shows a comparison of DBS elution conditions of 55° C. for 30 minutes vs. room temperature for 20 minutes at 1000 copies/mL of HIV-1. Seventy-one replicates per condition were used. (A) Cycle threshold (Ct) at 55° C. for 30 min was earlier than Ct at room temp for 20 minutes. (B) Maximum Ratio (MR; a measurement of signal strength) at 55° C. for 30 minutes was higher than MR at room temp for 20 minutes.
Figure 5B:
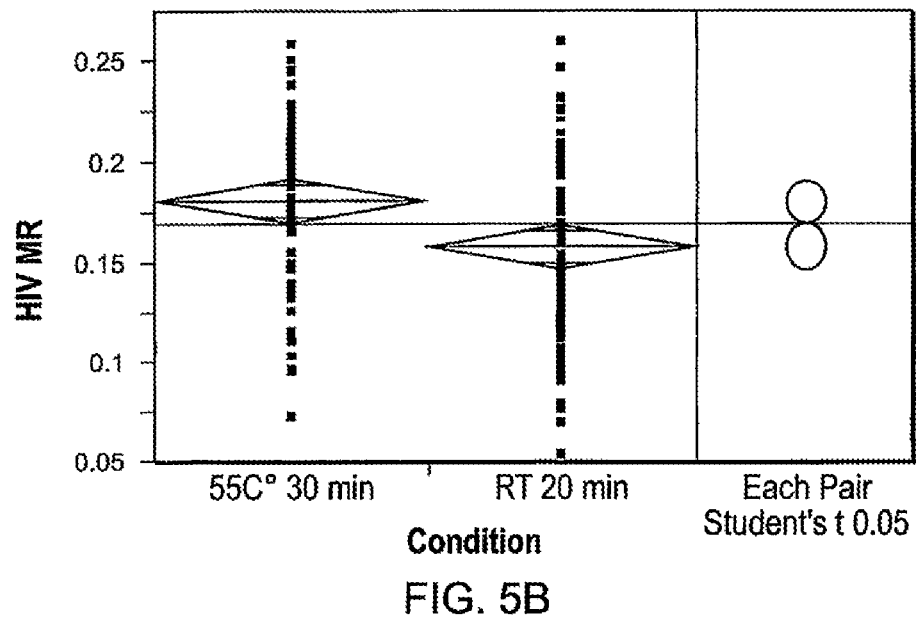
Figure 6A:
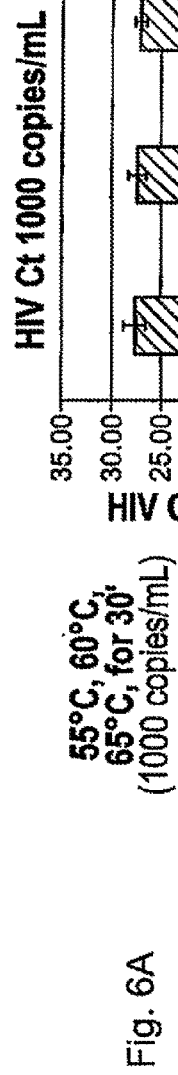
FIG. 6 (A-F) shows DBS elution at temperatures ranging from 52 to 65° C. from 25 to 45 minutes. While Ct values were comparable across the conditions, the condition with the highest MR value was 55° C. for 30 minutes. (A-C) HIV Ct; (A) 1000 copies/ml; (B) 3000 copies/ml; (C) 1250 copies/ml. (D-F) HIV MR, (A) 1000 copies/ml; (B) 3000 copies/ml; (C) 1250 copies/ml.
Figure 6B:
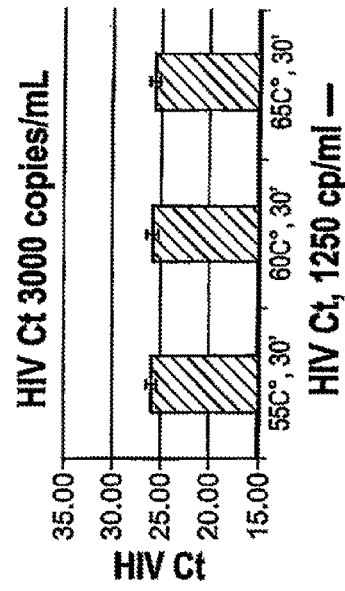
Figure 6C:
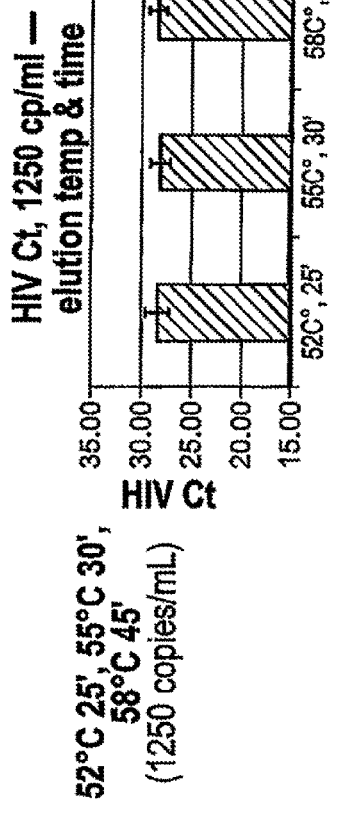
Figure 6D:
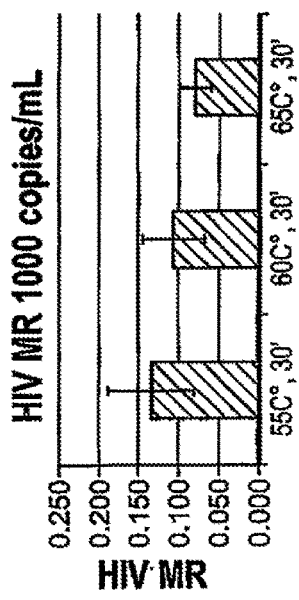
Figure 6E:
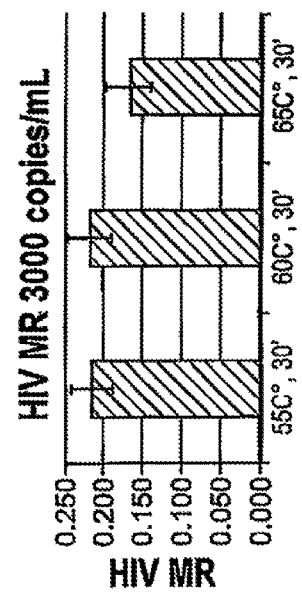
Figure 6F:
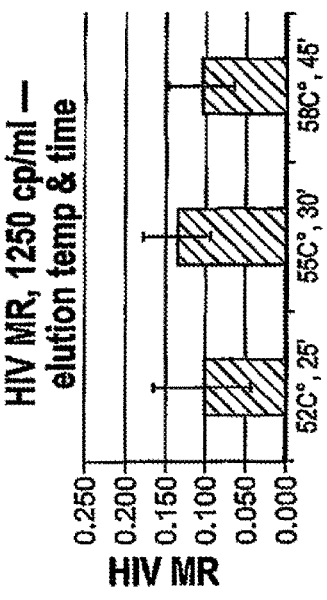
Figure 7D:
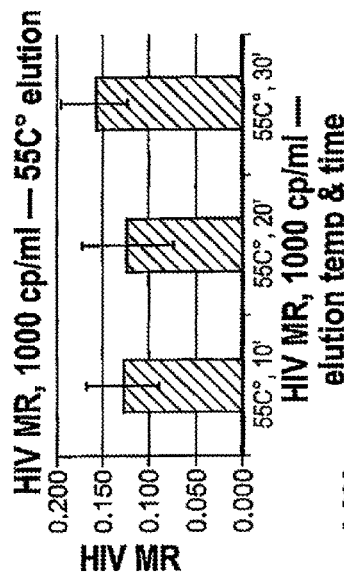
FIG. 7 (A-F) shows DBS elution at 55° C. for 10, 20, and 30 minutes. Increasing the elution time showed a trend to improve Ct and increase MR although the differences between each time point were not significant. After incubation at 55° C. for 30 minutes, further incubation at room temperature for up to 24 hours did not affect the PCR results. (A-C) HIV Ct; (A) 1000 copies/ml, SSC elution; (B) 1000 copies/ml; (C) 30 copies/ml. (D-F) HIV MR, (A) 1000 copies/ml, SSC elution; (B) 1000 copies/ml; (C) 3000 copies/ml.
Figure 7E:
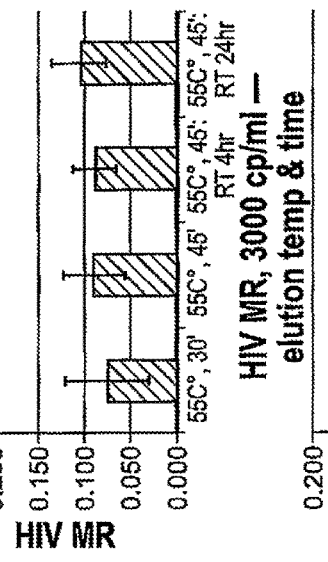
Figure 7F:
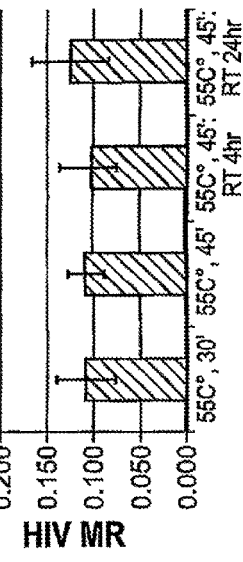

The assay sensitivity can also be improved by increasing elution efficiency. A direct comparison of room temperature for 20 minutes elution and 55° C. for 30 minutes elution was performed. The results (FIG. 5) suggested that both Ct (cycle threshold) and MR (maximum ratio) were improved significantly by increasing temperature to 55° C. for 30 minutes. The 55° C. temperature and timing were guard banded (FIGS. 6 and 7, respectively). The results (FIG. 6) showed that temperatures higher than 60° C. result in lower MR values. Overall, the highest MR was at 55° C. FIG. 7 showed that thirty minutes at 55° C. was required for more efficient DBS elution. After incubation at 55° C. for 30 minutes, further incubation at room temperature for up to 24 hours did not affect the PCR results. Furthermore, a comparison of RNA material recovered from DBS compared to whole blood directly spiked to sample buffer was conducted between room temperature for 20 minutes and 55° C. for 30 minutes. The results showed that the 55° C. elution condition increased the recovery by approximately 10% compared to the room temperature elution condition (Table 4). Continuous agitation of the DBS sample in buffer was combined with the 55° C. elution condition. The results showed slight improvement on the low HIV recovery from DBS; the improvement was not statistically significant (data not shown).

TABLE 4

Calculation of % recovery compared to whole blood

| | Ct mean | MR mean | Avg. % recovery compared to whole blood (range) |
|---|---|---|---|
| Condition 1000 copies/ml | | | |
| RT 20 min | 27.79 | 0.160 | 44.9 (34.1-62.8) |
| 55° C. 30 min | 27.43 | 0.180 | 57.4 (43.3-70.4) |
| Condition 250 copies/ml | | | |
| RT 20 min | 28.78 | 0.097 | 57.1 (40.6-68.9) |
| 55° C. 30 min | 28.59 | 0.103 | 66.1 (37.2-82.7) |

The improvement in percent recovery as compared to whole blood when the DBS were eluted at 55° C. for 30 minutes versus room temperature for 20 minutes was observed to be approximately 10%

A preliminary analytical sensitivity evaluation was conducted to estimate the sensitivity using a Virological Quality Assurance (VQA) HIV-1 dilution panel (panel lot #2) at 55° C. for 30 minutes. It was also tested using inactivated HIV-1 from SeraCare that was quantified using 3 lots of calibrators. The calibrators used for quantification were quantified using a VQA HIV-1 dilution panel (panel lot #1). The results are shown in Table 5. The LOD estimate is approximately 800 copies/mL.

TABLE 5

Sensitivity estimation

| HIV resource | HIV copies/ml | Number tested | Number detected | Percent detected | Logit LOD copies/ml | Probit LOD copies/ml |
|---|---|---|---|---|---|---|
| VQA 2 | 250 | 30 | 18 | 60 | 741 | 766 |
| | 500 | 30 | 24 | 80 | | |
| | 1000 | 30 | 30 | 100 | | |
| HIV LAV* | 250 | 16 | 11 | 68.8 | 884 | 865 |
| | 500 | 16 | 15 | 93.8 | | |
| | 1000 | 16 | 15 | 93.8 | | |

*Inactivated HIV-1 from SeraCare that was quantified using 3 lots of calibrator, which were quantified from VQA1.

Currently there are multiple commercially available DBS paper cards. It is important to show whether the performances are comparable. A study was conducted for side-by-side comparison of DBS paper cards by 3 different vendors. Multiple lots of paper cards were used if available. The results are summarized in Table 6. The performance based on low HIV concentration Ct, MR, and detection rate were similar. The differences were not statistically significant.

TABLE 6

Comparison of DBS paper from different vendors

| HIV cp/mL | Paper type/vendor lot number | Average HIV | | Detection rate |
|---|---|---|---|---|
| | | Ct | MR | |
| 1000 | Munktell TFN/LabMate lot 13-108-36 | 27.50 | 0.175 | 12/12 |
| 1000 | Munktell TFN/Lasec lot 13-108-24 | 27.14 | 0.202 | 12/12 |
| 1000 | Munktell TFN/Lasec lot 13-108-25 | 27.62 | 0.174 | 12/12 |
| 1000 | Ahlström 226/Perkin Elmer lot 103649 | 27.11 | 0.189 | 11/11 |
| 1000 | Whatman 903/GE Healthcare Lot 6933912 | 27.81 | 0.167 | 11/12 |

TABLE 6-continued

Comparison of DBS paper from different vendors

| HIV cp/mL | Paper type/vendor lot number | Average HIV Ct | MR | Detection rate |
|---|---|---|---|---|
| 1000 | Whatman 903/GE Healthcare Lot 6990814 | 27.41 | 0.174 | 12/12 |

We claim:

1. An automated method for detecting HIV-1 nucleic acids in a blood sample, the method comprising:
   a) providing: i) a blood sample suspected of being infected with HIV dried on a solid carrier, ii) an elution buffer, iii) an automated, programmable sample preparation instrument, iv) an automated, programmable PCR instrument v) PCR reagents suitable for detecting HIV-1 nucleic acids and, vi) optionally, DNase;
   b) eluting the blood sample from the solid carrier with the elution buffer to create an eluted sample;
   c) loading the eluted sample into the automated, programmable sample preparation instrument for further nucleic acid extraction and purification and extracting and purifying any nucleic acids to create a processed sample comprising extracted nucleic acids;
   d) loading the PCR reagents into the automated, programmable PCR instrument;
   e) initiating an automated program to aliquot the PCR reagents into the processed sample;
   f) performing PCR on the extracted nucleic acids in the processed sample with the automated, programmable PCR instrument; and
   g) analyzing PCR results generated by the automated, programmable PCR instrument to determine if any samples comprise HIV-1 nucleic acids;
   h) wherein, said elution buffer comprises approximately 3.5 M GITC, approximately 5% polysorbate 20, approximately 50 mM KOAc at approximately pH 6.0; and
   i) wherein, optionally, DNase is added to one or more of the processed sample, the PCR reagents, or the process sample comprising the PCR reagents.

2. The method of claim 1, wherein the method additionally comprises negative and positive controls.

3. The method of claim 1, wherein step b) is about 20 minutes at room temperature.

4. The method of claim 3, wherein step b) is performed with gentle intermittent mixing.

5. The method of claim 1, wherein step b) is about 30 minutes at about 55° C.

6. The method of claim 1, wherein step b) is performed with gentle intermittent mixing.

7. The method of claim 1, wherein said automated procedure is programmed by software commands.

8. The method of claim 1, wherein the method is performed with DNase and said DNase does not require specific DNase reaction buffers, is effective at ambient temperature or temperatures used during PCR cycling stages, effectively degrades DNA within the time period of 30 minutes, does not need to be inactivated after effectively degrading DNA and does not negatively impact the detection of RNA sequences.

9. The method of claim 1, wherein said solid carrier is filter paper.

10. The method of claim 1, wherein said nucleic acid is RNA.

11. The method of claim 1, wherein said nucleic acid is pro-viral HIV-1 DNA and wherein optional step i) of claim 1 is not performed.

12. The method of claim 1, wherein step b) is performed with continuous mixing.

* * * * *